(12) United States Patent
Shimizu et al.

(10) Patent No.: US 7,559,651 B2
(45) Date of Patent: Jul. 14, 2009

(54) OPHTHALMIC MEASUREMENT APPARATUS

(75) Inventors: Kazunari Shimizu, Gamagori (JP); Masanao Fujieda, Toyohashi (JP)

(73) Assignee: Nidek Co., Ltd., Gamagori-shi (JP)

( * ) Notice: Subject to any disclaimer, the term of this patent is extended or adjusted under 35 U.S.C. 154(b) by 80 days.

(21) Appl. No.: 11/979,325

(22) Filed: Nov. 1, 2007

(65) Prior Publication Data
US 2008/0174734 A1 Jul. 24, 2008

(30) Foreign Application Priority Data
Nov. 2, 2006 (JP) .............................. 2006-299156

(51) Int. Cl.
A61B 3/14 (2006.01)
A61B 3/10 (2006.01)
(52) U.S. Cl. ....................... 351/206; 351/211
(58) Field of Classification Search ................. 351/205, 351/206, 210–212, 221
See application file for complete search history.

(56) References Cited

U.S. PATENT DOCUMENTS 5,523,809 A 6/1996 Kohayakawa
5,907,388 A 5/1999 Fujieda
6,234,978 B1 5/2001 Mihashi et al.
7,270,413 B2 9/2007 Hirohara et al.
7,331,670 B2 * 2/2008 Ichikawa .................... 351/206

FOREIGN PATENT DOCUMENTS

JP A-2006-149871 6/2006

* cited by examiner

Primary Examiner—William C Choi
(74) Attorney, Agent, or Firm—Oliff & Berridge, PLC

(57) ABSTRACT

An ophthalmic measurement apparatus capable of outputting correction data (objective values) for a patient's eye as approximate as possible to subjective values includes an optical system for projecting a measurement target onto a fundus and detecting an image of the target reflected therefrom using a photoelectric element so as to obtain measurement data on eye refractive power distribution or wavefront aberration, an optical system for photographing an anterior-segment including a pupil using an image-pickup element, a device which detects a size of a pupil area by image processing, and a device which obtains a spherical power, an astigmatic power, and an astigmatic axial angle based on the data within a given area smaller than the pupil area when the detected size is larger than a reference size, and obtains the three values based on the data within the pupil area when the detected size is smaller than the reference size.

6 Claims, 2 Drawing Sheets

OPHTHALMIC MEASUREMENT APPARATUS

BACKGROUND OF THE INVENTION

1. Field of the Invention

The present invention relates to an ophthalmic measurement apparatus which measures eye refractive power distribution or wavefront aberration of a patient's eye.

2. Description of Related Art

Conventionally, there is known an apparatus which projects light in a spot shape (a measurement target) onto a fundus of a patient's eye (an examinee's eye) and detects information on wavefront of the light reflected from the fundus by using a wavefront sensor (photoelectric element) so as to measure wavefront aberration (especially, higher-order aberration) of the patient's eye (see U.S. Pat. No. 6,234,978 corresponding to Japanese Patent Application Unexamined Publication No. Hei 10-216092). In addition, there is known an ophthalmic apparatus which projects slit light onto a fundus of a patient's eye and detects the light reflected from the fundus by using a photoelectric element so as to measure the wavefront aberration or eye refractive power distribution of the patient's eye based on a signal indicating the phase difference at the time of the detection of the reflection light (see U.S. Pat. No. 5,907,388 corresponding to Japanese Patent Application Unexamined Publication No. Hei 10-108837).

Such an ophthalmic apparatus obtains information on optical characteristics (objective values) of the patient's eye based on known optical theory. However, a certain disagreement is developed between the obtained objective values and information on optical characteristics of the patient's eye which is obtained through subjective examination (subjective values). Such a disagreement is developed because the objective values are obtained based on the optical theory while the subjective values are influenced by the examinee's perception. In the case of making eye refractive power correction to prescribe spectacle lenses or contact lenses, the subjective values are obtained through the subjective examination on the basis of the objective values obtained by the ophthalmic apparatus as above or other apparatuses. Therefore, when using the objective values in preparing the spectacle lenses, data indicating values as approximate as possible to the subjective values is required in view of working efficiency.

SUMMARY OF THE INVENTION

An object of the invention is to provide an ophthalmic measurement apparatus capable of outputting correction data (data on objective values) for a patient's eye which is as approximate as possible to subjective values of the patient's eye.

To achieve the objects and in accordance with the purpose of the present invention, an ophthalmic measurement apparatus has a measurement optical system for projecting a measurement target onto a fundus of an examinee's eye and detecting an image of the measurement target reflected from the fundus by using a photoelectric element so as to obtain measurement data on eye refractive power distribution or wavefront aberration of the examinee's eye, a photographing optical system for photographing an anterior-segment including a pupil of the examinee's eye by using an image-pickup element, detection means which detects a size of a pupil area by processing the photographed image of the anterior-segment, and correction data calculating means which obtains a spherical power, an astigmatic power, and an astigmatic axial angle based on the measurement data within a given area which is smaller than the pupil area when the detected size of the pupil area is larger than a reference size, and obtains the spherical power, the astigmatic power, and the astigmatic axial angle based on the measurement data within the pupil area when the detected size of the pupil area is smaller than the reference size.

In another aspect of the present invention, an ophthalmic measurement apparatus has a measurement optical system for projecting a measurement target onto a fundus of an examinee's eye and detecting an image of the measurement target reflected from the fundus by using a photoelectric element so as to obtain measurement data on eye refractive power distribution or wavefront aberration of the examinee's eye, a photographing optical system for photographing an anterior-segment including a pupil of the examinee's eye by using an image-pickup element, and a central processing unit electrically connected to the image-pickup element, which detects a size of a pupil area by processing an image signal from the image-pickup element, compares the detected size of the pupil area with a reference size, calculates a spherical power, an astigmatic power, and an astigmatic axial angle based on the measurement data within a given area which is smaller than the pupil area when the detected size of the pupil area is larger than the reference size, and calculates the spherical power, the astigmatic power, and the astigmatic axial angle based on the measurement data within the pupil area when the detected size of the pupil area is smaller than the reference size.

Additional objects and advantages of the invention are set forth in the description which follows, are obvious from the description, or may be learned by practicing the invention. The objects and advantages of the invention may be realized and attained by the ophthalmic measurement apparatus in the claims.

BRIEF DESCRIPTION OF THE DRAWINGS

The accompanying drawings, which are incorporated in and constitute apart of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
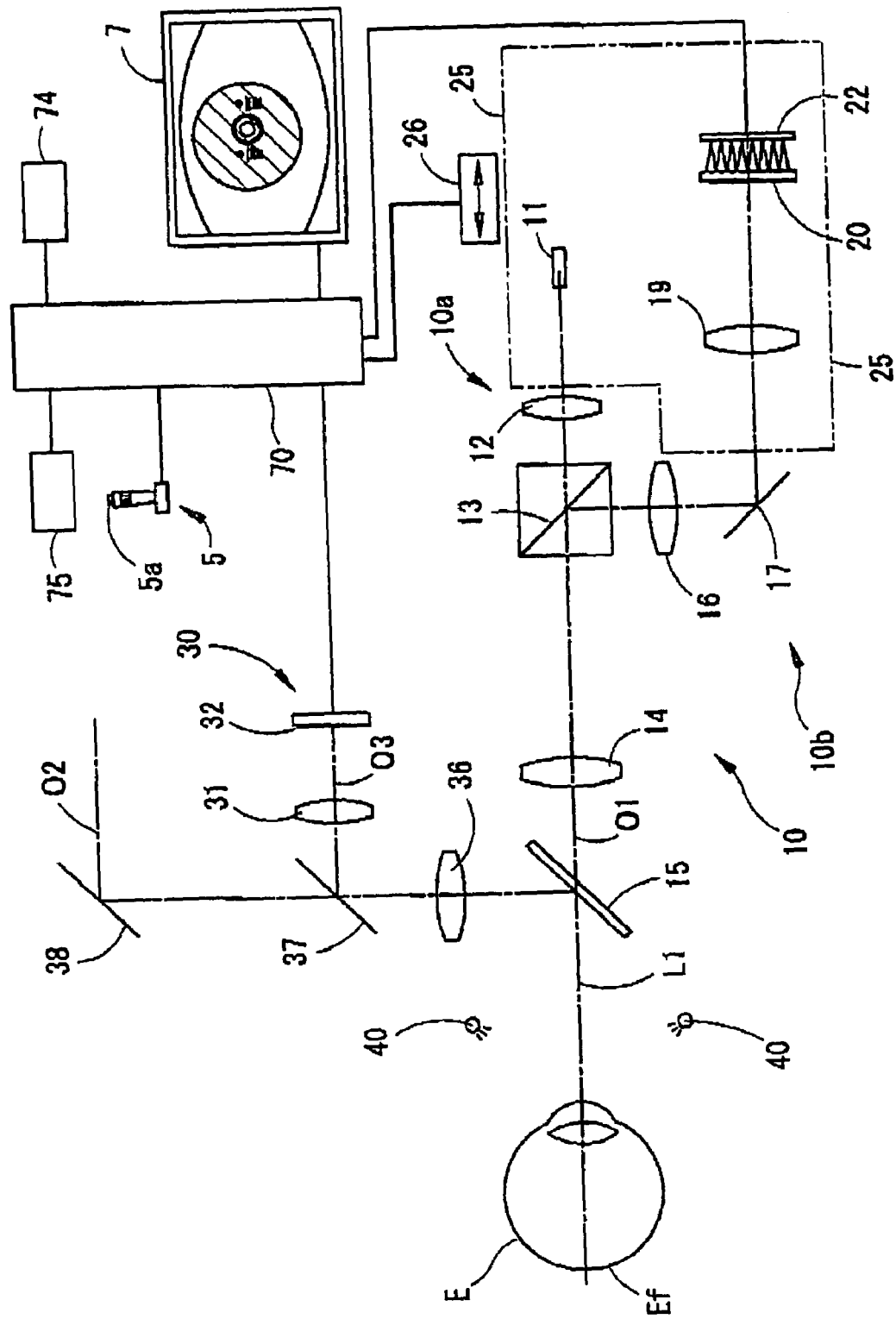
FIG. 1 is a view showing an optical system and a control system of an ophthalmic measurement apparatus according to a preferred embodiment of the present invention.

A detailed description of one preferred embodiment of an ophthalmic measurement apparatus embodied by the present invention is provided below with reference to the accompanying drawings. FIG. 1 is a view showing an optical system and a control system of the ophthalmic measurement apparatus according to the preferred embodiment of the present invention. A dichroic mirror 15 is placed in front of a patient's eye E. On a transmission optical path O1 of the dichroic mirror 15, a wavefront aberration measurement optical system 10 for measuring wavefront aberration of the patient's eye E is placed. The measurement optical system 10 includes a projection optical system 10a for projecting measurement light in a spot shape (a measurement target) which is emitted from a measurement light source 11 onto a fundus Ef, and a photo-receiving optical system 10b for dividing the measurement light reflected from the fundus Ef and emitted from the patient's eye E into a plurality of light bundles so as to photo-receive the light bundles on a two-dimensional photodetector (photoelectric element) 22. Based on output from the two-dimensional photodetector 22, the wavefront aberration of the patient's eye E is measured.

In the projection optical system 10a, a relay lens 12 and an objective lens 14 are placed in order in a direction from the measurement light source 11 to the patient's eye E. The measurement light source 11 is placed in a position conjugate with the fundus Ef. In the photo-receiving optical system 10b, the objective lens 14, a half mirror 13, a relay lens 16, a total reflection mirror 17, a collimator lens 19, a microlens array 20, and the two-dimensional photodetector 22 which photo-receives the light bundles passing through the microlens array 20 are placed in order from the front of the patient's eye E. The half mirror 13 transmits the measurement light from the measurement light source 11 and reflects the reflection light from the fundus Ef. The photo-receiving optical system 10b is arranged such that a pupil of the patient's eye E and the microlens array 20 have an optically conjugate relationship approximately. The microlens array 20 includes microlenses which are two-dimensionally arranged on a plane perpendicular to a measurement optical axis L1, and a light shielding plate. The microlens array 20 divides the reflection light from the fundus Ef into the plurality of light bundles. Incidentally, the photo-receiving optical system 10b in the preferred embodiment of the present invention is configured as a Shack-Hartmann wavefront sensor. Meanwhile, the photo-receiving optical system 10b may be configured as a Talbot wavefront sensor such that an orthogonal grid mask is placed in a position conjugate with a pupil so as to photo-receive light transmitted through the mask on a two-dimensional photodetector (see Japanese Patent Application Unexamined Publication No. 2006-149871).

In addition, in the preferred embodiment of the present invention, the measurement light source 11, the collimator lens 19, the microlens array 20 and the two-dimensional photodetector 22 are moved integrally as a unit 25 in a direction of the optical axis L1 by a moving mechanism 26. In this case, the unit 25 is moved in accordance with a spherical refractive error of the patient's eye E so that the measurement light source 11 and the two-dimensional photodetector 22 have an optically conjugate relationship with the fundus Ef. In other words, the unit 25 functions as a vision correcting mechanism for correcting the spherical refractive error of the patient's eye E.

In a reflecting direction of the dichroic mirror 15, an objective lens 36 used for observing the patient's eye E, a dichroic mirror 37 and a total reflection mirror 38 are placed. On an optical path O2 in a reflecting direction of the mirror 38, a fixation target projection optical system for making the patient's eye E fixate on a fixation target is placed (not illustrated).

On an optical path O3 in a reflecting direction of the dichroic mirror 37, a photographing optical system 30 for photographing the patient's eye E so as to obtain an image thereof is placed. The photographing optical system 30 includes an image forming lens 31, and a two-dimensional image-pickup element 32 such as an area CCD which is placed in a position approximately conjugate with the vicinity of an anterior-segment of the patient's eye E. Light sources 40 for anterior-segment illumination illuminate the anterior-segment of the patient's eye E with infrared light.

The dichroic mirror 15 has a property of transmitting light emitted from the measurement light source 11 included in the measurement optical system 10, and reflecting light (near infrared light) emitted from the anterior-segment illumination light sources 40 and a light source for alignment (not illustrated) and visible light. The dichroic mirror 37 has a property of transmitting the visible light and reflecting the near infrared light.

The light emitted from the anterior-segment illumination light sources 40 and reflected from the anterior-segment forms an image of the anterior-segment on the two-dimensional image-pickup element 32 via the dichroic mirror 15, the objective lens 36, the dichroic mirror 37 and the image forming lens 31. Fixation light emitted from the fixation target projection optical system is reflected by the mirror 38, travels on an optical path in the reverse direction to the direction in which the above-described anterior-segment reflection light travels on the optical path, and reaches the fundus Ef.

A control part 70 is a CPU (central processing unit) and is electrically connected with the two-dimensional photodetector 22. The control part 70 is programmed to obtain an image signal outputted from the two-dimensional photodetector 22 and analyze the wavefront aberration or other factors of the patient's eye E. Accordingly, the control part 70 acts as means for analyzing optical characteristics of the patient's eye E. The control part 70 is connected with the light source 11, the two-dimensional photodetector 22, a memory 75 acting as storing means, the moving mechanism 26, the two-dimensional image-pickup element 32, a display monitor 7 which displays the anterior-segment image of the patient's eye E and a measurement result, a joystick 5, and a control part 74 for performing various settings of the apparatus including measurement conditions.

Figure 2:
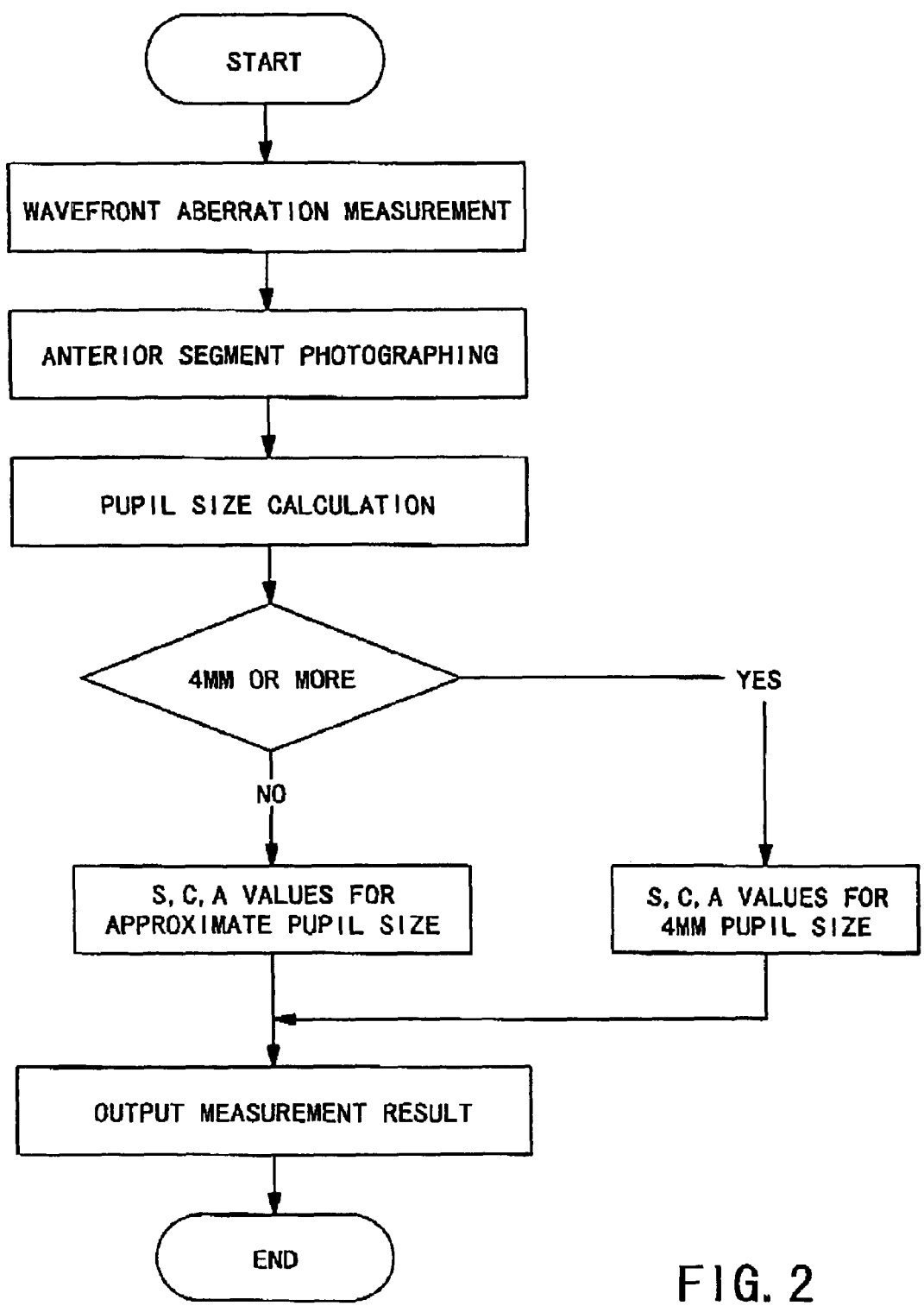
FIG. 2 is a flowchart concerning output of correction data performed by the ophthalmic measurement apparatus.

Hereinafter, a description of operation of the apparatus having the configuration as above will be given referring to a flowchart shown in FIG. 2. On the monitor 7, the anterior-segment image picked up by the two-dimensional image-pickup element 32 is displayed. An examiner moves an apparatus cabinet with the use of the joystick 5 while watching the monitor 7 so as to perform alignment of the measurement optical axis L1 with respect to the patient's eye E. After the alignment, a measurement starting switch 5a is pushed by the examiner so as to generate a trigger signal for measurement. Then, the control part 70 controls the measurement light source 11 to light up and starts measurement based on the trigger signal.

The measurement light emitted from the measurement light source 11 is projected onto the fundus Ef via the relay lens 12, the half mirror 13, the objective lens 14, the dichroic mirror 15, and the pupil of the patient's eye E. Thus, a point-light-source image is formed on the fundus Ef.

The measurement light, which is projected onto the fundus Ef so as to form the point-light-source image thereon and is reflected from the fundus Ef, is emitted from the patient's eye E and is transmitted through the dichroic mirror 15. Then, the transmitted measurement light is collected by the objective lens 14, is reflected by the half mirror 13, is once collected by the relay lens 16, and is reflected by the total reflection mirror 17. The light reflected by the total reflection mirror 17 passes through the collimator lens 19 and is divided into the plurality of light bundles by the microlens array 20 so as to be photo-received on the two-dimensional photodetector 22. A pattern image photo-received on the two-dimensional photodetector 22 is stored as image data in the memory 75.

The pattern image of the light bundles divided into which by the microlens array 20 and photo-received on the two-dimensional photodetector 22 varies with the degree of the aberration (low-order aberration and higher-order aberration) of the patient's eye E. Accordingly, by analyzing the pattern image which is formed by the reflection light from the patient's eye E with respect to a pattern image which is formed by aberration-free light, the wavefront aberration distribution and the eye refractive power distribution of the patient's eye E can be measured. At this time, the wavefront aberration distribution and the eye refractive power distribution may be measured by obtaining a plurality of pattern images with the use of the two-dimensional photodetector 22 and adding or averaging the pattern images.

After the measurement of the wavefront aberration, the control part 70 shifts to the photographing of the anterior-segment image. The control part 70 controls the anterior-segment illumination light sources 40 to light up and controls the two-dimensional image-pickup element 32 to obtain the anterior-segment image including the pupil of the patient's eye E which is illuminated by the anterior-segment illumination light sources 40. Then, the control part 70 controls the memory 75 to store the anterior-segment image obtained by the two-dimensional image-pickup element 32 as image data. Then, the control part 70 extracts a rim portion of the pupil of the patient's eye E from the anterior-segment image stored in the memory 75 through image processing, and detects a pupil diameter of the patient's eye E based on the extracted rim portion (i.e., the control part 70 acts as means for detecting a pupil area). Incidentally, for the detection of the pupil diameter of the patient's eye E, there is known a technique to detect pupil diameters in respective meridian directions and take an average value of the detected pupil diameters as the pupil diameter.

Next, the control part 70 obtains wavefront aberration W ($\rho, \theta$) based on an amount of displacements of dot images in the pattern image stored in the memory 75, and calculates a spherical power (S), an astigmatic power (C), and an astigmatic axial angle (A) based on the obtained wavefront aberration W ($\rho, \theta$). At this time, the control part 70 first judges whether or not the detected pupil diameter is equal to or larger than a pupil diameter P which is predetermined. Based on a result of the judgment, the control part 70 selects a calculation condition upon outputting correction data. For example, the pupil diameter P as a reference size is predetermined to be 4 mm, and the calculation condition is selected through a comparison to judge whether or not the detected pupil diameter is equal to or larger than 4 mm.

Here, a description of a case where the detected pupil diameter is equal to or larger than 4 mm will be given. The control part 70 obtains wavefront aberration data on the patient's eye which corresponds to an area of the predetermined pupil diameter P (4 mm) Then, the control part 70 calculates correction data (S,C,A values) for the patient's eye based on lower-order aberration calculated from the obtained wavefront aberration data. Next, a description of a case where the detected pupil diameter is smaller than 4 mm will be given. The control part 70 obtains wavefront aberration data on the patient's eye which corresponds to an area of the detected pupil diameter (for example, 3.5 mm), which is an actual size of the pupil of the patient's eye. Then, the control part 70 calculates correction data (S,C,A values) for the patient's eye based on lower-order aberration calculated from the obtained wavefront aberration data. That is to say, the control part 70 acts as correction data calculation means.

Hereinafter, a brief description of a process of calculating the correction data (S,C,A values) from the wavefront aberration W ($\rho, \theta$) will be given. Here, the wavefront aberration W ($\rho, \theta$) obtained based on the amount of the displacements of the respective dot images is quantified by applying expansion of the known Zernike's polynomials.

$$W(\rho,\theta) = \Sigma_{i=0} C_i Z_i$$

In this equation, $Z_i$ indicates the $i^{th}$ one of the Zernike's polynomials, and $C_i$ is a factor thereof. $\rho$ indicates a relative position with respect to the pupil diameter (in a range of 0 to 1), and $\theta$ indicates an angle which is measured counterclockwise with respect to the X axis (0 to $2\pi$). In a standard display type, the wavefront aberration W ($\rho, \theta$) is expressed by the following equations.

$$W(\rho, \theta) = \sum_n \sum_m C_n^m Z_n^m(\rho, \theta)$$

$$Z_n^m(\rho, \theta) = N_n^m R_n^m(\rho) \cos m\theta; \ 0 \le m$$

$$R_n^m(\rho) = \sum_{s=0}^{(n-|m|)/2} \{(-1)^s (n-s)!/s![0.5(n+|m|)-s]![0.5(n-|m|)-s]!\} \rho^{n-2s}$$

In addition, the normal constant is expressed by the following equation.

$$N_n^m = \sqrt{2(n+1)/(1+\delta_{m0})}$$

Incidentally, a result of the analysis of the wavefront aberration can be displayed in the form of a map on the monitor 7.

The spherical power (S), the astigmatic power (C), and the astigmatic axial angle (A) are expressed in terms of polynomials of degree two or lower.

$$S = -4\sqrt{3} \cdot C_2^0 / R^2$$

$$C = -4\sqrt{6} \cdot \sqrt{(C_2^{-2})^2 + (C_2^2)^2} \Big/ R^2$$

$$A = \tan^{-1}\left(\frac{C_2^{-2}}{C_2^2}\right) \cdot \frac{1}{2} \cdot \frac{180}{\pi} + 90$$

In these equations, R indicates the radius (mm) of the pupil diameter to be analyzed. Besides, higher-order aberrations are expressed in terms of polynomials of degree three or higher.

If the detected pupil diameter is equal to or larger than 4 mm, the wavefront aberration W ($\rho, \theta$) is calculated by using the value of the predetermined pupil diameter P (4 mm) which is used as the judging criteria. In calculating the correction data (S,C,A values), the following relational expression is used.

$$R = P/2$$

On the other hand, if the detected pupil diameter is smaller than 4 mm, the wavefront aberration W ($\rho, \theta$) is calculated by using a value of a detected pupil diameter CL which is the pupil diameter of the patient's eye. In calculating the correction data (S,C,A values), the following relational expression is used.

$$R = CL/2$$

Thereafter, the control part 70 outputs the calculated correction data (S,C,A values) for the patient's eye as measurement values. For example, the correction data is outputted by displaying it on the monitor 7. Alternatively, the correction data may be outputted by printing it out by using a printer (not illustrated), or by transmitting it to an electric phoropter for subjective examination.

By the configuration as above, when the pupil diameter of the patient's eye is equal to or larger than the predetermined value, the S,C,A values are outputted based on the wavefront aberration data which is obtained by using the predetermined value. On the other hand, when the pupil diameter of the patient's eye is smaller than the predetermined value, the S,C,A values are outputted based on the wavefront aberration data which corresponds to the detected pupil diameter. Accordingly, the correction data for the patient's eye is calculated from the wavefront aberration data in accordance with the pupil diameter as approximate as possible to the predetermined pupil diameter.

Based on knowledge obtained empirically through experiments, the S,C,A values calculated from the wavefront aberration data in the case of the pupil diameter being 4 mm are approximate to subjective values. Therefore, the S,C,A values are calculated from the wavefront aberration data in the case of the pupil diameter being 4 mm if possible Otherwise, in the case of the pupil diameter being smaller than 4 mm, the S,C,A values are calculated from the wavefront aberration data in accordance with the pupil diameter being approximate to 4 mm. Accordingly, it becomes possible to output the correction data which is as approximate as possible to the subjective values.

Though the present inventors have empirically judged that the correction data calculated for the pupil diameter of 4 mm is approximate to the subjective values, this is not limited in particular. It is also preferable that the predetermined value of the pupil diameter used as the judgment criteria in calculating the S,C,A values from the wavefront aberration can be adjusted or varied. For example, a switch for varying the predetermined value may be provided to the control part 74 so as to enable the examiner to arbitrarily adjust or vary the predetermined value. By doing so, the predetermined value can be varied according to the judgment of each examiner. Therefore, it becomes possible to output the correction data which is more appropriate.

Incidentally, the present inventors have focused attention on that the pupil diameter of the patient's eye at the time of the calculation of the correction data does not necessarily correspond to a pupil diameter of a healthy individual in a normal life environment. In addition, the present inventors have focused attention on the size of the pupil of the healthy individual in the normal life environment, and set the size of the pupil diameter which is considered to be approximate to the size of the pupil of the healthy individual in the normal life environment (for example, 4 mm) as the predetermined pupil diameter, so that the measurement values approximate to the subjective values can be obtained. In addition, even if the pupil diameter does not reach the predetermined pupil diameter, the measurement values approximate to the subjective values can be outputted since the correction data for the area approximate to the predetermined pupil diameter is calculated.

Incidentally, it is also preferable that a predetermined pupil diameter for day vision and a predetermined pupil diameter for night vision are respectively set as the size of the pupil diameter which is considered to be approximate to the size of the pupil diameter of the healthy individual in the normal life environment, and correction data for day vision and correction data for night vision are outputted in accordance with the measurement condition. For example, considered is a technique to take 4 mm as the predetermined value of the pupil diameter for day vision, and take 6 mm as the predetermined value of the pupil diameter for night vision.

In the above description, the S,C,A values are calculated from the wavefront aberration data of the patient's eye. However, it is also preferable that eye refractive powers are respectively obtained at a plurality of corneal portions in meridian directions, and the S,C,A values in the area approximate to the predetermined pupil diameter are calculated from data on the respective refractive powers. An ophthalmic measurement apparatus capable of calculating the eye refractive powers at the plurality of corneal portions in the meridian directions includes an ophthalmic measurement apparatus having a measurement optical system for projecting a measurement target onto the fundus of the patient's eye and photo-receiving light formed by the measurement target and reflected from the fundus, which uses a phase-difference method (see U.S. Pat. No. 5,907,388 corresponding to Japanese Patent Application Unexamined Publication No. Hei10-108837) or a multiple ring method (see U.S. Pat. No. 5,523,809 corresponding to Japanese Patent Application Unexamined Publication No. Hei6-121773). In such a case, when the pupil diameter of the patient's eye is equal to or larger than the predetermined pupil diameter, the S,C,A values are outputted based on the eye refractive power data obtained in the area which corresponds to the predetermined pupil diameter. On the other hand, when the pupil diameter of the patient's eye is smaller than the predetermined pupil diameter, the S,C,A values are outputted based on the eye refractive power data obtained in the area approximate to the detected pupil diameter.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic measurement apparatus comprising:
   a measurement optical system for projecting a measurement target onto a fundus of an examinee's eye and detecting an image of the measurement target reflected from the fundus by using a photoelectric element so as to obtain measurement data on eye refractive power distribution or wavefront aberration of the examinee's eye;
   a photographing optical system for photographing an anterior-segment including a pupil of the examinee's eye by using an image-pickup element;
   detection means which detects a size of a pupil area by processing the photographed image of the anterior-segment; and
   correction data calculating means which obtains a spherical power, an astigmatic power, and an astigmatic axial angle based on the measurement data within a given area which is smaller than the pupil area when the detected size of the pupil area is larger than a reference size, and obtains the spherical power, the astigmatic power, and the astigmatic axial angle based on the measurement data within the pupil area when the detected size of the pupil area is smaller than the reference size.

2. The ophthalmic measurement apparatus according to claim 1, wherein the reference size of the pupil area is an actual size of the pupil of the examinee's eye.

3. The ophthalmic measurement apparatus according to claim 1, wherein the reference size of the pupil area is set respectively for day vision and night vision.

4. An ophthalmic measurement apparatus comprising:

a measurement optical system for projecting a measurement target onto a fundus of an examinee's eye and detecting an image of the measurement target reflected from the fundus by using a photoelectric element so as to obtain measurement data on eye refractive power distribution or wavefront aberration of the examinee's eye;

a photographing optical system for photographing an anterior-segment including a pupil of the examinee's eye by using an image-pickup element; and a central processing unit electrically connected to the image-pickup element, which detects a size of a pupil area by processing an image signal from the image-pickup element, compares the detected size of the pupil area with a reference size, calculates a spherical power, an astigmatic power, and an astigmatic axial angle based on the measurement data within a given area which is smaller than the pupil area when the detected size of the pupil area is larger than the reference size, and calculates the spherical power, the astigmatic power, and the astigmatic axial angle based on the measurement data within the pupil area when the detected size of the pupil area is smaller than the reference size.

5. The ophthalmic measurement apparatus according to claim 4, wherein the reference size of the pupil area is an actual size of the pupil of the examinee's eye.

6. The ophthalmic measurement apparatus according to claim 4, wherein the reference size of the pupil area is set respectively for day vision and night vision.

* * * * *